United States Patent [19]

Longley

[11] Patent Number: 4,499,028

[45] Date of Patent: Feb. 12, 1985

[54] PREPARATION OF ISETHIONIC ACID

[75] Inventor: Kermit D. Longley, Park Forest, Ill.

[73] Assignee: Witco Chemical Corporation, New York, N.Y.

[21] Appl. No.: 415,119

[22] Filed: Sep. 7, 1982

[51] Int. Cl.³ .................. C07C 143/02; C07C 143/16
[52] U.S. Cl. .............................. 260/513 R; 260/429.9
[58] Field of Search ......................... 260/513 R, 429.9

[56] References Cited

U.S. PATENT DOCUMENTS

| | | | |
|---|---|---|---|
| 2,547,906 | 4/1951 | Fincke | 260/513 R |
| 2,597,696 | 5/1952 | Anthes et al. | 260/513 R |
| 3,167,570 | 1/1965 | Bohanek et al. | 269/400 |
| 3,888,918 | 6/1975 | Kuehnhanss | 260/513 R |

FOREIGN PATENT DOCUMENTS

| | | |
|---|---|---|
| 848463 | 9/1960 | United Kingdom . |
| 1059984 | 2/1967 | United Kingdom . |

OTHER PUBLICATIONS

Chemical Abstracts 98 (1) 4301v (1983).

*Primary Examiner*—Helen M. S. Sneed
*Attorney, Agent, or Firm*—Wallenstein, Wagner, Hattis, Strampel & Aubel

[57] ABSTRACT

A method for the preparation of isethionic acid by treating an alkali metal isethionate with hydrochloric acid to form isethionic acid and a chloride salt. The chloride salt is removed so as to provide at least a 50% by weight aqueous solution of the isethionic acid after removal of excess hydrochloric acid, which solution may be further reacted with a polyvalent metal oxide, hydroxide or amine to form the corresponding heavy metal isethionate. Zinc isethionate, for instance, is useful as a catalyst for making acyl isethionates used in making soap bars.

7 Claims, No Drawings

PREPARATION OF ISETHIONIC ACID

FIELD OF INVENTION

This invention relates to making isethionic acid and prepariing a polyvalent metal isethionate therefrom.

BACKGROUND AND DISCUSSION OF THE PRIOR ART

Isethionic acid also bears the chemical nomenclature of 2-hydroxy ethanesulfonic acid.

Heretofore, isethionic acid has been prepared by the hydrolysis of ethionic acid or carbyl sulfate, products which result from the reaction of two moles of sulfur trioxide with one mole of ethanol or ethylene, respectively. However, these preparations resulted in the formation of an equimolar amount of undesired sulfuric acid. Another approach proposed the reaction of a large excess of ethylene with sulfur trioxide to give an oligomer $(C_2H_4)_{1.0}(SO_3)_{1.14}$ that can then be hydrolyzed to isethionic acid containing less sulfuric acid than the previous reaction.

It was also known to produce carboxylic acid esters of hydroxy-alkane-sulfo acids by mixing a carboxylic acid with a metal salt hydroxy-alkane-sulfo acid and passing gaseous hydrogen chloride through the mixture, as disclosed in U.S. Pat. No. 3,167,570, granted Jan. 26, 1965 to Bohanek, et al.

Zinc isethionate, for instance, was recognized as being useful as one of a number of metal salt catalysts in the preparation of acyl isethionates in Great Britain Patent No. 848,463, published Sept. 14, 1960, to Van Alphen, et al. Generally, metal sakIt isethionates had been commercially prepared from ammonium isethionate as discussed in Chem Abstracts 67 63797r and Great Britain Pat. No. 1,059,984.

Now there is provided by the present invention an improved method of producing isethionic acid in a form which is readily converted into the corresponding polyvalent metal isethionate, which may be used as such, in solution, for numerous applications, for instance, as a catalyst.

It is therefore a principal object of the present invention to provide a novel method for the preparation of isethionic acid.

It is a further object of the present invention to provide a method as aforesaid wherein a heavy metal isethionate may be readily produced from the isethionic acid.

It is a further object of the present invention to provide a method as aforesaid in which by-product sulfuric acid is avoided in preparing the isethionic acid.

It is still a further object of the present invention to provide a method as aforesaid which the amount of water present is at a minimum.

It is still a further object of the present invention wherein the by-products of the isethionic acid reaction are readily removed.

It is still another object of the present invention to produce the heavy metal isethionate which is useful as a catalyst.

The aforesaid, as well as other objects and advantages, will become apparent from a reading of the following description, and the adjoined claims.

DESCRIPTION OF THE PREFERRED EMBODIMENTS

Broadly speaking, the present invention comprises mixing an alkali metal isethionate with anhydrous hydrochloric acid or a concentrated hydrochloric acid solution to form isethionic acid in solution and precipitate the alkali metal chloride, provided that the alkali metal isethionate is in a substantially saturated aqueous solution where the hydrochloric acid is anhydrous (hydrogen chloride), and the alkali metal isethionate is in a dry state where the hydrochloric acid is in a concentrated solution. The water content should not be more than 35% of the combined water and sodium isethionate.

The product is filtered then stripped to remove the excess hydrochloric acid so as to preferably achieve a 50% or better aqueous solution of isethionic acid. However, lower concentrations may be employed successfully, but because of the excess dilution, are not particularly preferred. The isethionate acid in solution is readily reacted with a polyvalent heavy metal compound to produce the corresponding heavy metal isethionate.

In the preparation of the isethionic acid, it is important that the amount of water present in the reaction be at a minimum to insure the ready precipitation and removal of the by-product chloride salt.

Suitable alkali metal isethionate starting reactants include, sodium, potassium and lithium, with sodium being preferred.

Concentrated aqueous hydrochloric acid when employed should be at least about 30% by weight, and preferably 35% or greater, and a molar excess of hydrochloric acid should be employed to ensure complete reaction so as to obtain isethionic acid. Specifically, the sodium isethionate should be present in about 65% by weight on the basis of the sum of the water and isethionate, 1.3 moles of hydrochoric acid being present per mole of sodium isethionate.

The reaction may be kept below about 70° C., and as low as about room temperature, for several hours to obtain an easily filterable chloride crystal. Generally, the process is preferably conducted between about 25° C. and 70° C. for about 1 to 10 hours.

Separation of the precipitated chloride salt is then made by procedures known in the art including filtration and fractionation with a solvent such as isopropanol. The isethionic acid solution is concentrated to about from 40% to about 80% by weight. This concentrated solution is then readily combined with a polyvalent metal compound at room temperature or at a higher temperatures if necessary to form the corresponding salt in aqueous solution. The solution may be used, per se, or it may be crystalized by procedures well known to one skilled in the art.

Suitable polyvalent metal compounds include, for instance, calcium, barium, magnesium, cadmium, lead, tin and zinc. in the form of their oxides, hydroxides and amines, or the free metal such as tin, may be used. The most prefered Group II metal compounds are the zinc compounds.

Zinc isethionate, for instance, is useful as a catalyst in the preparation of acyl isethionates, which are incorporated in soap bar compositions, which is readily prepared by the present process.

The following Examples are illustrative of the present invention.

EXAMPLE I

To 444 lbs. (4.50 moles) of 36% concentrated aqueous hydrochloric acid was added 491 lbs. (3.32 moles) of dry commercial sodium isethionate over a period of about 1 hour at room temperature. After the addition was complete, the mixture was stripped for an additional four hours to complete the reaction.

The aqueous solution was filtered from precipitated chloride salt, and this salt was reslurried in 64 lbs. of isopropanol. The liquid was separated by filtration and the salt discharged to the sewer.

The two liquid product fractions above were combined and transferred to a glass-lined still. The excess water, isopropanol and hydrochloric acid were removed by heating to 90° C. under vacuum.

The light yellow syrupy product weighing 411 lbs. was analyzed as follows:
80% Isethionic Acid
9% Sodium Isethionate
11% Water

EXAMPLE II

A sample of 860 lbs. of a commercial grade aqueous sodium isethionate (57.2% solution-3.32 moles) was transferred to a glass-lined vessel and heated under vacuum to concentrate to a 65% solution. The concentrated solution was then cooled to 40° C.

To the above solution was added 160 lbs. (4.50 moles of anhydrous gaseous hydrochloric acid over a period of eight hours while maintaining the temperature below 70° C. by cooling as needed.

When the addition was complete, the reaction mixture was cooled and the salt removed by filtration. The filtrate was transferred to a glass-lined still and the excess water and hydrochloric acid removed by heating under vacuum to 90° C.

Recovery was 482 lbs. of an almost colorless syrup with the following analysis:
70% Isethionic Acid
26% Water
3.7% Sodium Isethionate
0.01% Sodium Chloride It will be understood that the foregoing examples and explanation are for illustrative purposes and that the present invention includes numerous modifications which will be self-evident to those skilled in the art. Accordingly, the invention is not to be limited save as is consonant with the following claims.

The embodiments of the invention in which an exlusive property or privilege is claimed are defined as follows:

1. A method for preparation of isethionic acid comprising;
forming a reaction mixture consisting essentially of an alkali metal isethionate and a molar excess of hydrochloric acid, the hydrochloric acid being in the form of anhydrous gaseous hydrogen chloride or a concentrated aqueous solution, the alkali metal isethionate being in the form of a substantially saturated aqueous solution when the hydrochloric acid is anhydrous, and the alkali metal isethionate being in a substantially dry state when the hydrochloric acid is in the form of a concentrated aqueous solution, and reacting the alkali metal isethionate with the hydrochloric acid to form isethionic acid.

2. The method of claim 1, said concentrated aqueous hydrochloric acid being at least about 30% by weight.

3. The method of claim 2, said alkali metal being sodium.

4. The method of claim 1, wherein the alkali metal isethionate is present in about 65% by weight in solution in the reaction mixture.

5. The method of claim 4, wherein there is 1.3 moles of hydrochloric acid to 1 mole of alkali metal isethionate in the reaction mixture.

6. The method of claim 5, wherein the product isethionic acid is present in at least about 50% by weight.

7. The method of claim 6, comprising the further step of removing the chloride salt by-product formed during the reaction and concentrating the isethionic acid formed in the reaction mixture.

* * * * *